(12) United States Patent
Araki et al.

(10) Patent No.: US 7,329,724 B2
(45) Date of Patent: Feb. 12, 2008

(54) PHARMACEUTICALLY STABLE HEMOSTATIC COMPOSITIONS

(75) Inventors: Tatsuya Araki, Kumamoto-ken (JP); Kazuhiko Tomokiyo, Kumamoto-ken (JP); Yasushi Nakatomi, Kumamoto-ken (JP); Kaori Teshima, Kumamoto-ken (JP); Tomohiro Nakagaki, Kumamoto-ken (JP)

(73) Assignee: Juridical Foundation the Chemo-Sero-Therapeutic Research Institute, Kumamoto-Ken (JP)

( * ) Notice: Subject to any disclaimer, the term of this patent is extended or adjusted under 35 U.S.C. 154(b) by 59 days.

(21) Appl. No.: 10/483,427

(22) PCT Filed: Jul. 10, 2002

(86) PCT No.: PCT/JP02/06982

§ 371 (c)(1),
(2), (4) Date: Jan. 12, 2004

(87) PCT Pub. No.: WO03/006054

PCT Pub. Date: Jan. 23, 2003

(65) Prior Publication Data

US 2004/0147439 A1    Jul. 29, 2004

(30) Foreign Application Priority Data

Jul. 10, 2001 (JP) ............................. 2001-209921

(51) Int. Cl.
*A61K 38/00* (2006.01)

(52) U.S. Cl. .................. 530/300; 530/350; 530/300; 435/7.1; 514/2

(58) Field of Classification Search .................. None
See application file for complete search history.

(56) References Cited

FOREIGN PATENT DOCUMENTS

WO    WO 91/09641        7/1991
WO    WO 01/47548 A1     7/2001

OTHER PUBLICATIONS

Mohan Rao et al. (PNAS, vol. 85, pp. 687-6691, 1988).*

* cited by examiner

*Primary Examiner*—Hope Robinson
(74) *Attorney, Agent, or Firm*—Browdy and Neimark, PLLC

(57) ABSTRACT

A novel hemostatic composition and a hemostatic pharmaceutical preparation are provided. A pharmaceutically stable hemostatic liquid composition comprising a mixed solution of activated blood coagulation factor VII (FVIIa) and blood coagulation factor X (FX) in a single container. The mixed solution is maintained at pH ranging from 5.0 to 6.5.

5 Claims, 3 Drawing Sheets

Fig. 1 Coagulation cascade; Roman numerals denote coagulation factors, "a" represents their active form. PL: Phospholipids ated blood coagulation factor VII (hereinafter also referred to as "FVIIa") and blood coagulation factor X (hereinafter also referred to as "FX") in a single container.

PHARMACEUTICALLY STABLE HEMOSTATIC COMPOSITIONS

TECHNICAL FIELD

The present invention belongs to the field of medical drugs and relates to a novel hemostatic composition comprising plasma proteins and a pharmaceutical preparation thereof. More specifically, the present invention relates to a medicament for treatment comprising a mixed solution of activated blood coagulation factor VII (hereinafter also referred to as "FVIIa") and blood coagulation factor X (hereinafter also referred to as "FX") in a single container.

BACKGROUND ART

Hemostasis in patients suffering from hemophilia with inhibitor has been managed with activated prothrombin complex concentrates (APCCs) or recombinant activated blood coagulation factor VII (rFVIIa). However, neither of these agents are satisfactory in view of safety for the former agents and in view of efficacy for the latter agents. To obviate these disadvantages, the present inventors disclosed in Japanese Patent Publication No. 2001-181204 (Japanese Patent Application No. 368122/1999) that a pharmaceutical composition comprising FVIIa and FX is useful as a hemostatic.

A pharmaceutical composition comprising as an active ingredient proteins for hemostatic management is most suitably administered intravenously in a dosage form appropriate for application via a container such as an ampoule, a syringe or a vial in which the composition is contained. More generally, a set of two containers has been used, one containing lyophilized proteins and the other containing a solution for dissolving said lyophilized proteins. A concentrate of proteins relating to blood coagulation factors, said proteins being prepared from plasma or by using the genetic recombination technique, has been formulated to a pharmaceutical preparation wherein most of said preparation has been provided as a set of lyophilized powder of proteins and a dissolving solution.

SUMMARY OF THE INVENTION

There are two options for devising a dosage form of the preparation comprising FVIIa and FX. One option is to provide FVIIa and FX each in separate containers while the other is to provide a mixture of FVIIa and FX in a single container. In accordance with the latter option, a single set of a mixture of lyophilized powder of both proteins and a dissolving solution will result, thus necessitating two containers in total. On the other hand, the former option will require a separate set of a lyophilized powder of protein and a dissolving solution each for both proteins, thus necessitating four containers in total. Moreover, additional device or manipulation of transferring a dissolving solution to a container of a lyophilized powder of protein will be necessary in case of the former option. In this regard, the former option is disadvantageous in view of facility. Thus, if both FVIIa and FX could be mixed together to be contained in a single container, a pharmaceutical preparation possessing not only pharmacological usefulness but also pharmaceutical facility would be obtained.

As shown in FIG. 1, FVIIa and FX are related to each other as an enzyme and its substrate. Under physiological conditions, FVIIa forms a complex with a tissue factor occurring on the vascular lesion in the presence of phospholipids and $Ca^{2+}$ to activate FX. The resulting activated FX (FXa) triggers the subsequent enzymatic reactions to lead to a final hemostasis by forming an insoluble fibrin. FXa is indeed an effective factor exhibiting hemostatic effect when produced at topical hemorrhage on the vascular lesion. However, it is reported that FXa may induce systemic hypercoagulability when FXa is present in an excessive amount in circulation (British Journal of Haematology 69: 491-497 (1988)). It is suggested that FXa may also be involved in induction of inflammation via activation of vascular endothelial cells or mesangial cells (Proc. natl. Sci. USA 97: 5255-5260 (2000); J. Am. Soc. Nephrol. 12: 891-899 (2001)).

A hydrolysis of FX by FVIIa producing FXa cannot be regulated when both FX and FVIIa proteins are present at a high concentration to thereby produce a large amount of FXa. Besides, the resulting FXa may hydrolyze FVIIa as a substrate to thereby inactivate FVIIa (Journal of Biological Chemistry 248: 7729-7741 (1973)). As such, it is extremely difficult to provide a mixture of FX and FVIIa in a stable solution. In such an unstable state, the mixture may not be formulated to a pharmaceutical preparation nor administered to patients.

Hitherto, there have been no known preparations wherein a mixture of an enzyme and its substrate, each purified and prepared, is contained in a single container as no techniques to overcome the above-described problems have been established.

Under the circumstances, the present inventors have earnestly investigated to develop a dosage form in which the enzyme FVIIa and its substrate FX are mixed together in a single container. As a result, the present inventors surprisingly have found out a method for preparing a mixed composition which stably comprises a mixture of the enzyme and its substrate as well as a pharmaceutical composition thereof, and based on this finding, have completed the present invention.

Namely, the present invention provides a liquid composition comprising FVIIa and FX in a single container wherein FVIIa is mixed with FX at an acidic pH ranging from 5.0 to 6.5, which is out of a pH range of from 6.5 to 10.0, i.e. the optimum pH of FVIIa, as well as a lyophilized preparation of said composition for use as a hemostatic medicament.

The present invention relates to a liquid composition comprising a mixture of FVIIa and FX and a lyophilized preparation of said composition. A principal feature of the present invention lies in regulating said liquid composition at a specific pH range of acidity. For this purpose, any buffer solution may be used in the present invention insofar as it may regulate the liquid composition at a specific pH range of acidity. An exemplary buffer solution that may be utilized includes, for instance, an acetate buffer, a tartrate buffer, a citrate buffer, and the like.

DETAILED DESCRIPTION OF THE INVENTION

Figure 1:
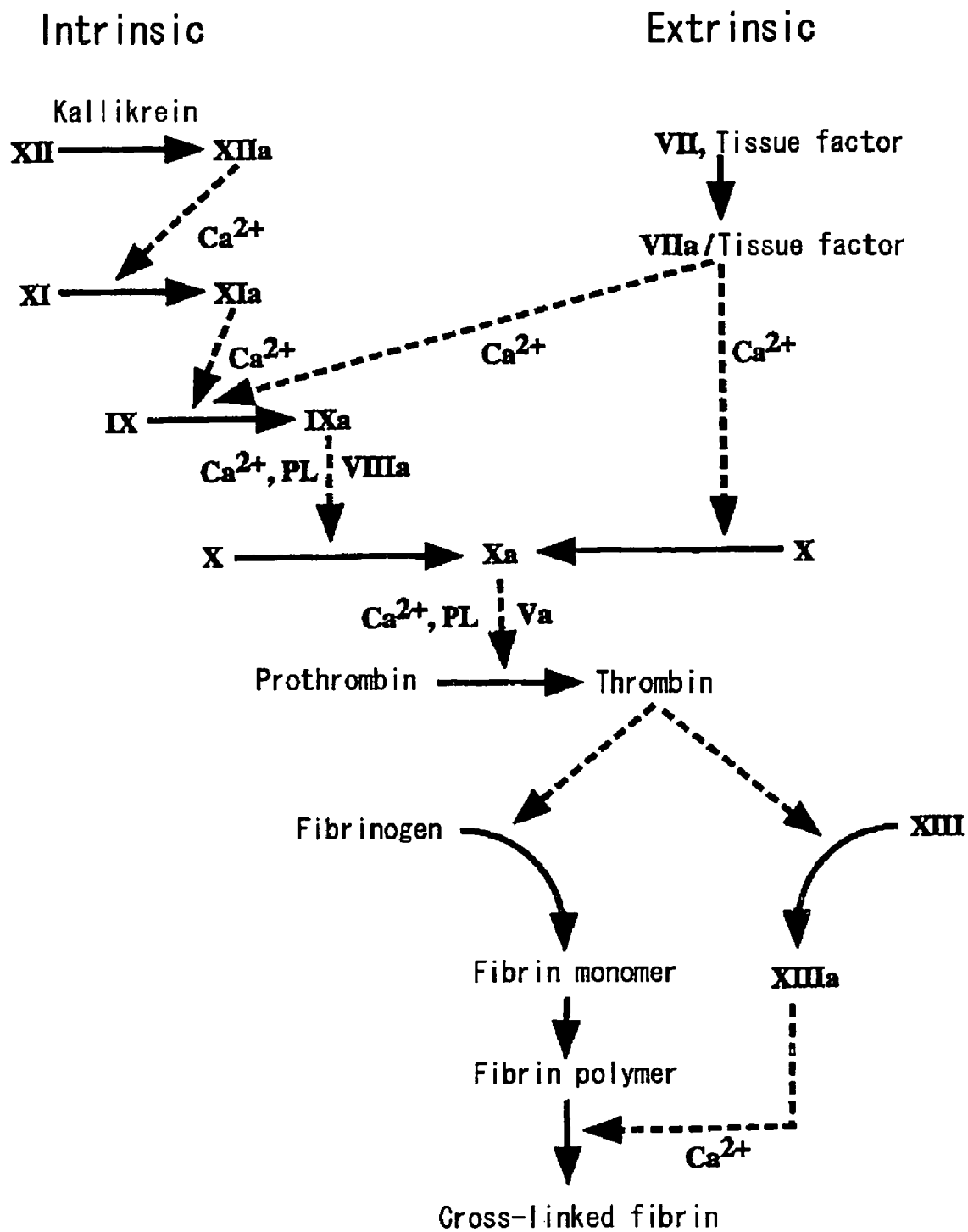
FIG. 1 shows a blood coagulation cascade consisting of two pathways, i.e. intrinsic and extrinsic.

A buffer may suitably be prepared at pH ranging from 5.0 to 10.0. At pH more acidic than this range, stability of FVIIa and/or FX in the solution will be impaired wherein FVIIa and/or FX are gradually inactivated. At pH more basic than this range, stability of FVIIa and/or FX in the solution is also not sufficient and hence the proteins are inactivated gradually. At pH 6.5 to 10.0, however, the substrate FX is converted into FXa by FVIIa. Therefore, pH ranging from 5.0 to 6.5, preferably from 5.4 to 6.1, may be used, by which there is no concern about impairment of the activity of each component or conversion from FX into EXa.

FVIIa and FX for use in the present invention may be prepared by any known methods, for example, by isolating from human blood or by the genetic recombination technique.

FVIIa may be prepared from blood by the known methods including those disclosed in e.g. Japanese Patent Publication No. 155797/1991, Japanese Patent Publication No. 059866/1998 and Japanese Patent-Publication No. 059867/1998. Alternatively, FVIIa may be prepared by applying cryo-poor plasma, which is prepared by cool-thawing human fresh frozen plasma and removing cryoprecipitate by centrifugation, to anion exchange chromatography to give crude FVII, which is then purified by affinity column chromatography with immobilized anti-FVII monoclonal antibody, followed by activation of FVII with other plasma proteins such as activated blood coagulation factor XII, or EXa. To ensure safety, the resulting FVIIa may preferably be contaminated with as little prothrombin, thrombin, FIX and FIXa as possible.

FX may be prepared from blood by applying cryo-poor plasma, which is prepared by cool-thawing human fresh frozen plasma and removing cryoprecipitate by centrifugation, to anion exchange chromatography to give crude FX, which is then purified by affinity column chromatography with immobilized anti-FX monoclonal antibody. Like in case of FVIIa, to ensure safety, the resulting FX may preferably be contaminated with as little prothrombin, thrombin, FIX and FIXa as possible.

The liquid composition of the present invention may suitably comprise FVIIa at 1 to 20 µM and FX at 5 to 400 µM. In a preferable embodiment, the liquid composition of the present invention may additionally comprise 0.001 to 1% by weight non-ionic surfactant, and not less than 0.01% by weight of one or more compounds selected from the group consisting of albumin, sugars and amino acids, to thereby allow for storage stability of the composition as well as to facilitate dissolution at reconstitution in case that said liquid composition is lyophilized.

The composition or the hemostatic preparation of the present invention may be administered to any patients who suffer from various hemostatic disorders and demonstrate hemorrhagic inclination.

The present invention provides a novel hemostatic preparation with improved safety, efficacy and facility.

The present invention is explained in more detail by means of the following Examples which are not intended to restrict the scope of the present invention in any sense.

EXAMPLE 1

In order to investigate stability of a FVIIa/FX mixture in a buffer solution, 0.4 mg/mL FVIIa and 1.0 mg/mL FX were mixed together in a buffer solution (MES buffer in the absence of $CaCl_2$: 100 mM MES, 100 mM NaCl) at specified pH and the mixture was incubated at 37° C. The activity of each FVIIa, FX and FXa in a sample was measured at each specified time in a system where any of these factors does not affect to each other. FVIIa used herein was a blood-derived product prepared as described in Japanese Patent Publication No. 155797/1991.

Figure 2:
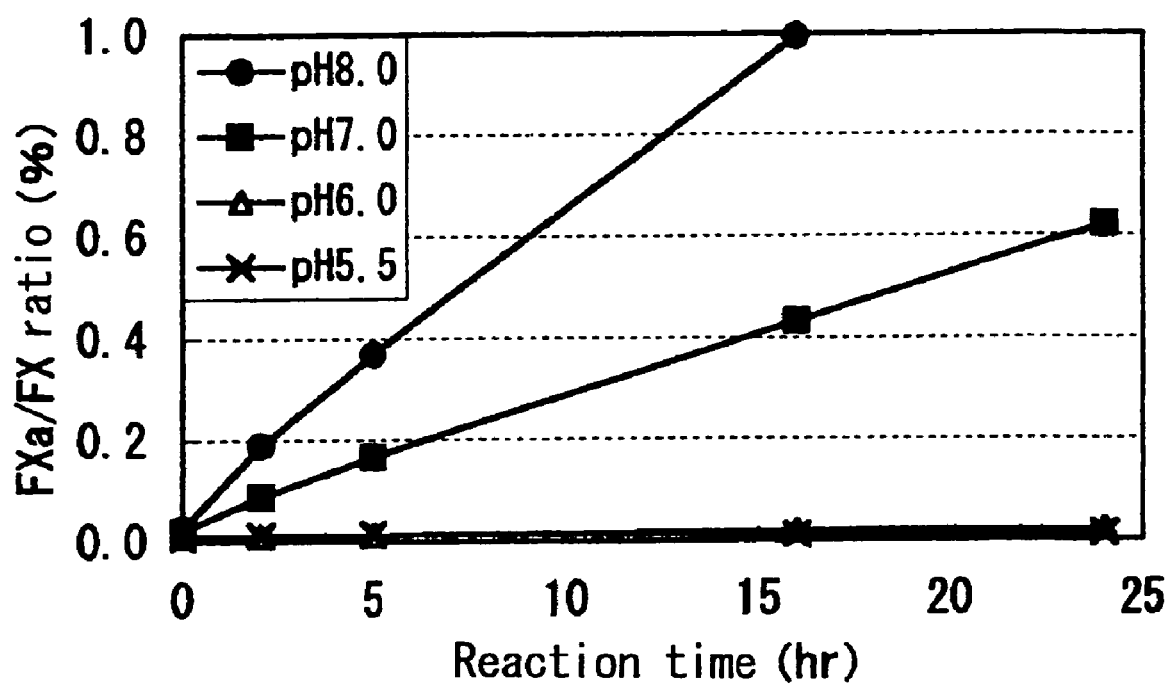
FIG. 2 shows a level of FXa produced, if any, in a liquid composition of the present invention comprising a mixture of FVIIa and FX at several values of pH.

As a result, both FVIIa and FX retained more than 90% activity after incubation for 24 hours at every pH values of the buffer tested. A content of FXa was calculated on the basis of its specific hydrolytic activity to a synthetic substrate (S2222) and a molar ratio of the content to FX is shown in FIG. 2. No increase in a content of FXa was observed in the buffer at pH 5.6 and 6.0 while drastic increase in a content of FXa was detected in the buffer at pH 7.0 and 8.0.

EXAMPLE 2

In order to investigate stability of a FVIIa/FX mixture in a buffer solution after lyophilization, 0.4 mg/mL FVIIa and 1.0 mg/mL FX were mixed together in a buffer solution [citrate buffer in the absence of $CaCl_2$: 10 mM sodium citrate, 120 mM NaCl, 0.5% glycine, 2% albumin, and 50 ppm TWEEN® 80(polysorbate 80)] at specified pH to prepare a bulk, which was lyophilized. As in Example 1, FVIIa used herein was a blood-derived product prepared as described in Japanese Patent Publication No. 155797/1991.

Figure 3:
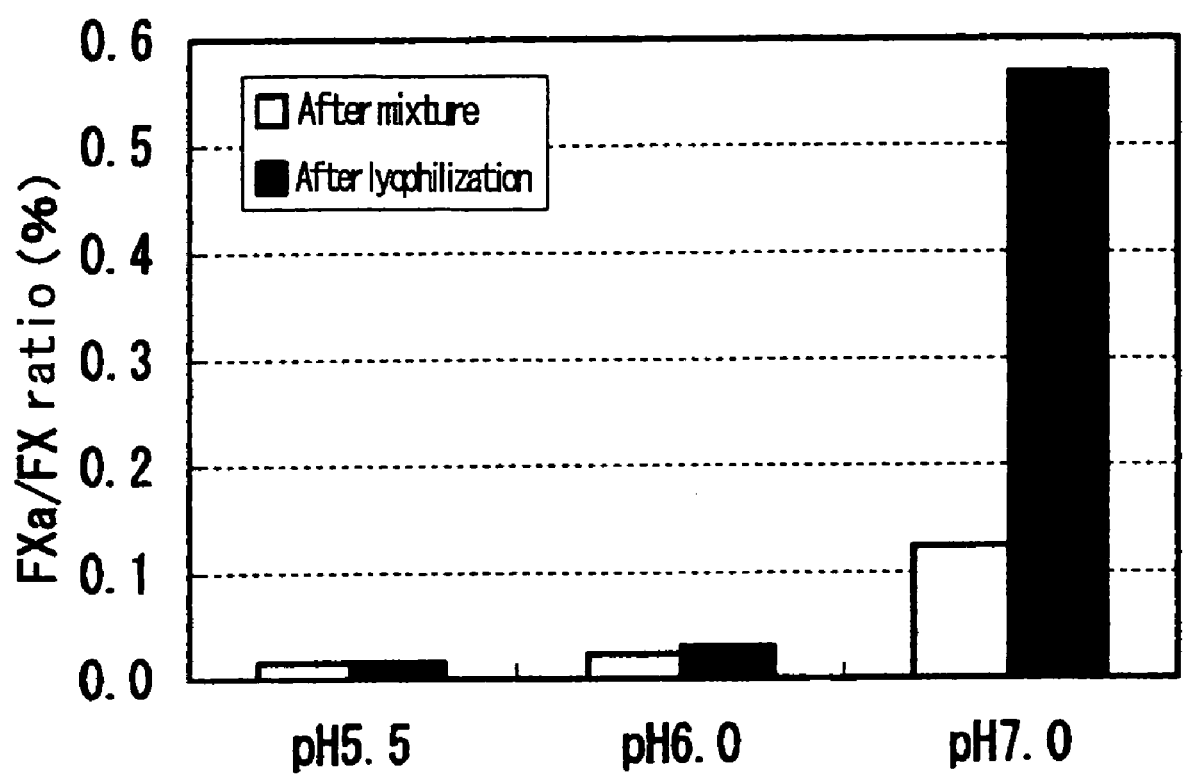
FIG. 3 shows a level of FXa produced, if any, in a lyophilized preparation of the present invention comprising a mixture of FVIIa and FX at several values of pH before and after lyophilization.

The activity of each factor was measured before and after lyophilization as described in Example 1 and the content of FXa is shown in FIG. 3. As a result, both FVIIa and FX retained more than 80% activity before and after lyophilization at every pH value of the buffer tested. No increase in a content of FXa was observed in the buffer at pH 5.5 and 6.0 while drastic increase in a content of FXa was detected in the buffer at pH 7.0.

The invention claimed is:

1. A pharmaceutically stable hemostatic liquid composition comprising a mixed solution of activated Factor VII (FVIIa) and Factor X (FX) in a pharmaceutically acceptable carrier in a single storage container, wherein the pH of the solution ranges from 5.0 to 6.5.

2. The pharmaceutically stable hemostatic liquid composition of claim 1 wherein said composition comprises FVIIa at 1 to 20 µM and EX at 5 to 400 µM.

3. A lyophilized hemostatic pharmaceutical preparation which is prepared by lyophilizing the pharmaceutically stable hemostatic liquid composition as set forth in claim 1.

4. A method for stabilizing a liquid composition comprising a mixed solution of FVIIa and FX in a single container, which comprises adjusting said liquid composition to a pH ranging from 5.0 to 6.5 and maintaining said liquid composition at said pH.

5. A lyophilized hemostatic pharmaceutical preparation which is prepared by lyophilizing the pharmaceutically stable hemostatic liquid composition as set forth in claim 2.

* * * * *